United States Patent
Wood et al.

(10) Patent No.: US 9,579,185 B2
(45) Date of Patent: Feb. 28, 2017

(54) IMPLANTABLE MEDICAL DEVICES FOR REDUCED TISSUE INFLAMMATION

(71) Applicant: BOSTON SCIENTIFIC SCIMED, INC., Maple Grove, MN (US)

(72) Inventors: Mark Wood, Shrewsbury, MA (US); Dane T. Seddon, Boston, MA (US); Sean Fleury, Brighton, MA (US); Daniel Ross, Watertown, MN (US); Burns P. Doran, Monticello, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 14/190,343

(22) Filed: Feb. 26, 2014

(65) Prior Publication Data
US 2014/0243974 A1  Aug. 28, 2014

Related U.S. Application Data

(60) Provisional application No. 61/770,905, filed on Feb. 28, 2013.

(51) Int. Cl.
*A61F 2/04* (2013.01)
*A61F 2/24* (2006.01)
(Continued)

(52) U.S. Cl.
CPC .............. *A61F 2/04* (2013.01); *A61F 2/2418* (2013.01); *A61F 2/82* (2013.01); *A61F 2/915* (2013.01); *A61F 2/91* (2013.01); *A61F 2230/0006* (2013.01); *A61F 2230/0008* (2013.01); *A61F 2250/0036* (2013.01); *A61F 2250/0098* (2013.01)

(58) Field of Classification Search
CPC ........ A61F 2/82; A61F 2002/825; A61F 2/86; A61F 2002/9155; A61F 2/2418
See application file for complete search history.

(56) References Cited

U.S. PATENT DOCUMENTS 5,238,004 A   8/1993 Sahatjian et al.
5,741,327 A   4/1998 Frantzen
(Continued)

FOREIGN PATENT DOCUMENTS

DE   102010009802 A1 * 9/2011 ............. A61F 2/915
EP   1974700 A1   10/2008
(Continued)

OTHER PUBLICATIONS

International Search Report, International Application No. PCT/US2014/018538, Boston Scientific Scimed, Inc., May 27, 2014 (5 pgs.).

*Primary Examiner* — Katrina Stransky
*Assistant Examiner* — Daniel Bissing
(74) *Attorney, Agent, or Firm* — Seager, Tufte & Wickhem, LLP

(57) ABSTRACT

Implantable medical devices and methods for making and using the same are disclosed. An example implantable medical device may include a stent having a first configuration and a second expanded configuration. The stent may define a plurality of nodes. The stent may have a cover member disposed adjacent the nodes. The cover member may be configured to cover at least some of the nodes when the stent is in the expanded configuration.

6 Claims, 17 Drawing Sheets

(51) Int. Cl.
*A61F 2/82* (2013.01)
*A61F 2/915* (2013.01)
*A61F 2/91* (2013.01)

(56) References Cited

U.S. PATENT DOCUMENTS

| | | |
|---|---|---|
| 6,508,803 B1 | 1/2003 | Horikawa et al. |
| 7,563,277 B2 | 7/2009 | Case et al. |
| 7,740,653 B1 | 6/2010 | Pollock et al. |
| 7,993,387 B2 | 8/2011 | Clerc et al. |
| 2008/0243230 A1 | 10/2008 | Lootz et al. |
| 2009/0171438 A1 | 7/2009 | Chuter et al. |
| 2011/0093061 A1 | 4/2011 | Lootz et al. |
| 2011/0166640 A1 | 7/2011 | Leewood et al. |
| 2011/0319989 A1* | 12/2011 | Lane ............ A61F 2/2418 623/2.11 |
| 2013/0090713 A1* | 4/2013 | Nissl ............ A61F 2/915 623/1.2 |

FOREIGN PATENT DOCUMENTS

| | | |
|---|---|---|
| WO | 9639102 A1 | 12/1996 |
| WO | 20080011175 A2 | 1/2008 |

* cited by examiner

IMPLANTABLE MEDICAL DEVICES FOR REDUCED TISSUE INFLAMMATION

CROSS-REFERENCE TO RELATED APPLICATIONS

This application claims priority under 35 U.S.C. §119 to U.S. Provisional Application Ser. No. 61/770,905, filed Feb. 28, 2013, the entirety of which is incorporated herein by reference.

TECHNICAL FIELD

The present disclosure pertains to medical devices, and methods for making and using medical devices. More particularly, the present disclosure pertains to implantable medical devices for reduced tissue inflammation.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device may include an implantable medical device such as a stent. The stent may have a first configuration and a second expanded configuration. The stent may define a plurality of nodes. The stent may have a cover member disposed adjacent the plurality of nodes. The cover member may be configured to cover at least some of the plurality of nodes when the stent is in the expanded configuration.

Another example implantable stent may include a stent body having a plurality of nodes including a first node, a second node, and a third node. The second node may be positioned between the first node and the third node. A cover member may be attached to the first node and attached to the third node. The cover member may extend over and cover the second node.

An example method for reducing inflammation caused by a stent may include providing an implantable stent. The stent may comprise a stent body having a plurality of nodes including a first node, a second node, and a third node. The second node may be disposed between the first node and the third node. A cover member may be attached to the first node, may be attached to the third node, and may extend over the second node.

The method may also include expanding the stent body and implanting the stent in a body lumen.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
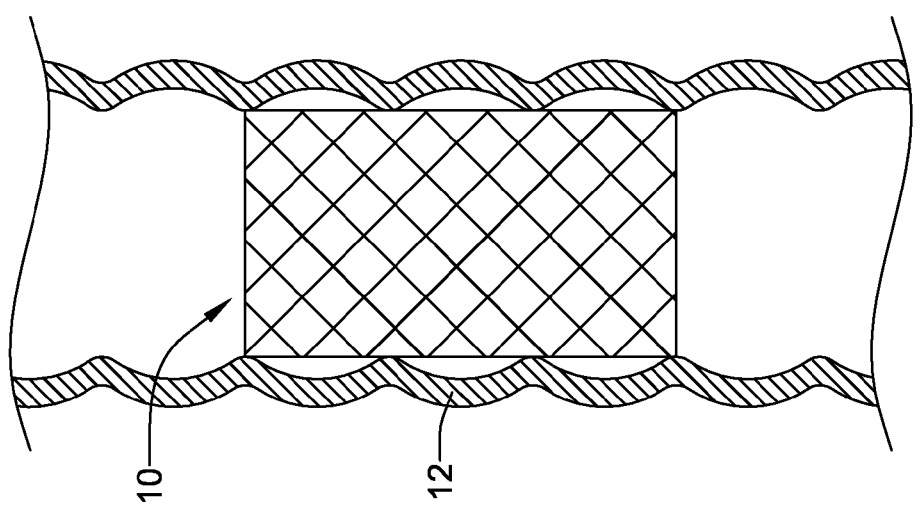
FIG. 1 is a plan view of an example implantable medical device disposed within a body lumen.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

The use of a stents, endoprostheses, implants, or the like may be a used to open or otherwise maintain the patency of the body lumen. For example, intravascular occlusions may be treated by implanting a stent within the blood vessel. Similarly, other body lumens including those along the digestive tract as well as along airways may also be treated in a similar manner. It can be appreciated that some body lumens may have a tendency to move. For example, peristalsis along portions of the digestive tract and/or along the esophagus may cause these body lumens to move. Similarly, the airways also move due to breathing, coughing, etc. A stent implanted along such regions could be subjected to forces that could cause the stent to elongate and/or shorten. This could lead to rubbing, pinching, poking, or general irritation at places where the stent and/or the relatively "sharp" edges of the stent contact the anatomy (e.g., along the mucous membrane or other tissues layer(s) in the lumen). In some cases, this could lead to inflammation, formation of granulation tissue, pain, or damage to the body lumen. Over an extended period of time, such irritation could lead to a number of different undesired consequences including reduced lumen patency, increased removal difficulty, greater mucus plugging, infection, or the like. Disclosed herein are example implantable devices such as stents that may help to reduce irritation, inflammation, or the like to body lumens. Such stents/implants may be well suited for implantation along body lumens that have a tendency to move or otherwise may be subjected to deformation forces.

FIG. 1 illustrates an example implant 10 disposed in a body lumen 12. In this example, implant 10 may take the form of a stent or endoprosthesis. In other embodiments, the structure and/or form of stent 10 may vary. In addition, body lumen 12 is shown schematically in this example and may represent the esophagus. This, however, is not intended to be limiting as body lumen 12 may represent a variety of different body lumens including those along the digest tract, along an airway, a blood vessel, etc. In some instances, body lumen 12 may be subjected to movement caused, for example, by peristalsis, breathing, coughing, or the like. When this happens, portions of stents like stent 10 may be expanded, shortened, or otherwise deformed. This could lead to rubbing, pinching, etc. of the anatomy, particularly along the ends or edges of the stent, which ultimately could cause inflammation and/or formation of granulation tissue. Stent 10 may include one or more structural features that help reduce inflammation and/or formation of granulation tissue. Some examples of the structural features that may be utilized to reduce inflammation and/or formation of granulation tissue are disclosed herein.

Figure 2:
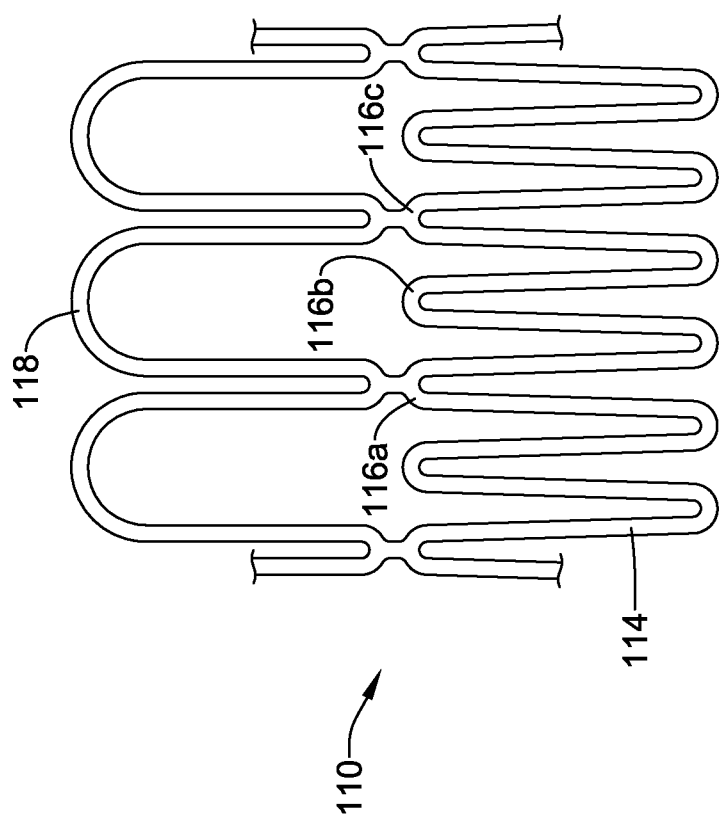
FIG. 2 is a side view of a portion of an example implantable medical device in a first configuration.
Figure 3:
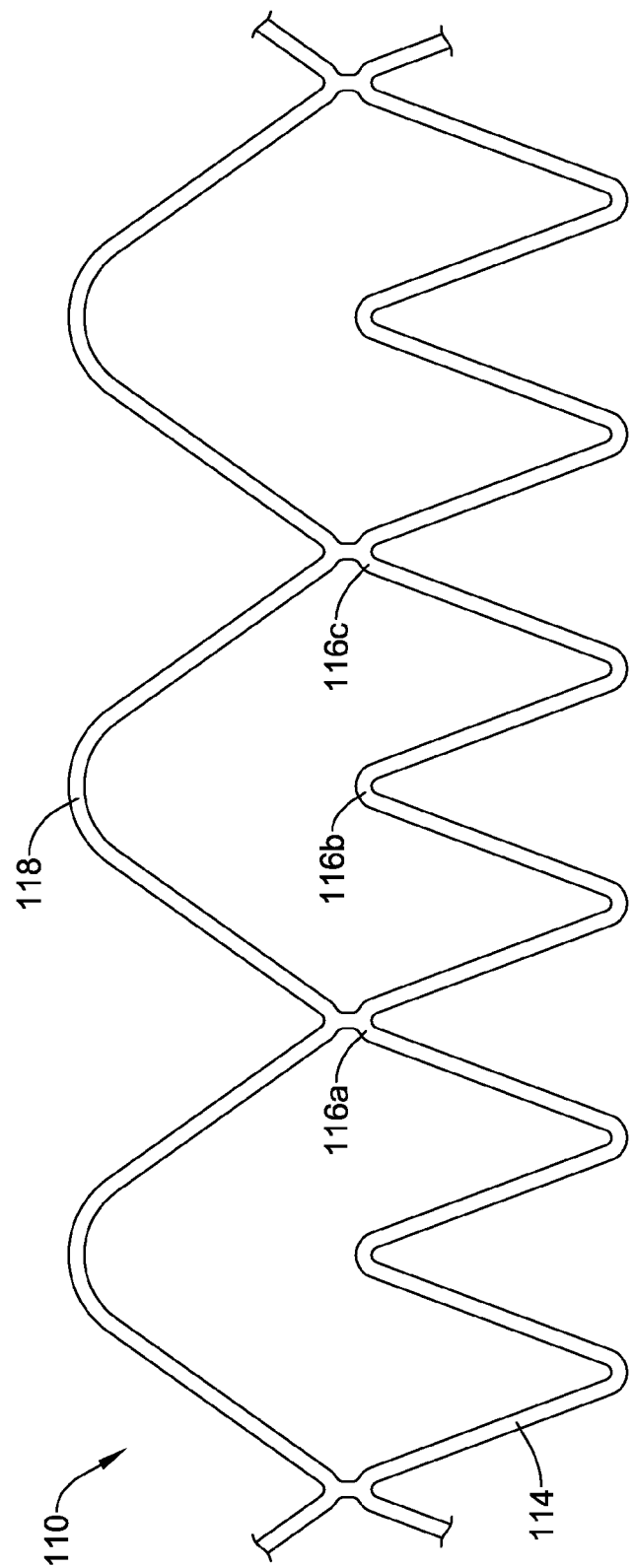
FIG. 3 is a side view of a portion of the example implantable medical device shown in FIG. 2 in a second configuration.

FIGS. 2-3 illustrate a portion of an example stent 110. In FIG. 2, stent 110 is shown in a first or "unexpanded" configuration. In FIG. 3, stent 110 is shown in a second or "expanded" configuration. Stent 110 may have a stent body or mesh-like structure 114. Accordingly, body 114 may have a generally cylindrical/tubular shape with a structure that resembles a braid, mesh, or matrix. It can be appreciated that for simplicity purposes, only a portion of body 114 is shown. Body 114 may define a plurality of stent edges or nodes defined therein such as nodes 116a/116b/116c. The number of nodes 116a/116b/116c may vary. In at least some embodiments, the number of nodes 116a/116b/116c may vary depending on the shape, size/diameter, length, or other physical dimensions of body 114. In general, nodes 116a/116b/116c may resemble points or pointed edges that may be disposed along the length of body 114. It can be appreciated, however, that a wide variety of shapes and/or configurations are contemplated for nodes 116a/116b/116c. At least some of these shapes contemplated for nodes 116a/116b/116c may be described as pointed, triangular, C-shaped, U-shaped, or the like. These are just examples.

A cover member 118 may be coupled to body 114. In general, cover member 118 may be configured to be disposed adjacent to one or more of nodes 116a/116b/116c. Accordingly, cover member 118 may aid in blocking or shielding the anatomy from any somewhat "pointed" edges of nodes 116a/116b/116c that may be present along body 114. For example, cover member 118 may be attached to node 116a and to node 116c. In at least some embodiments, cover member 118 may extend over node 116b. Thus, cover member 118 may "cover" node 116b, which may help reduce the likelihood of node 116b pinching, poking, or otherwise irritating the anatomy. In addition, the attachment of cover member 118 to nodes 116a/116b may also help shield or otherwise reduce the likelihood of these nodes 116a/116b irritating the anatomy as well.

Forming stent 110 may include providing a tubular body and cutting the body into the desired configuration. This may include laser cutting the tube to define the stent body (e.g., body 114). For efficiency, for example, it may be desirable to cut the tubular body so as to define the stent body in a relatively "compact" or unexpanded configuration (e.g., similar to stent 110 and/or stent body 114 as shown in FIG. 2). In some embodiments, it may be desirable to expand or otherwise alter the shape of the stent prior to implanting. This may include disposing the stent onto a mandrel or suitable expanding structure to deform the stent body into a relatively "larger" or expanded configuration (e.g., similar to stent 110 and/or stent body 114 as shown in FIG. 3). When "expanded", stent 110 may be delivered and implanted within the desirable portion of the anatomy.

Figure 4:
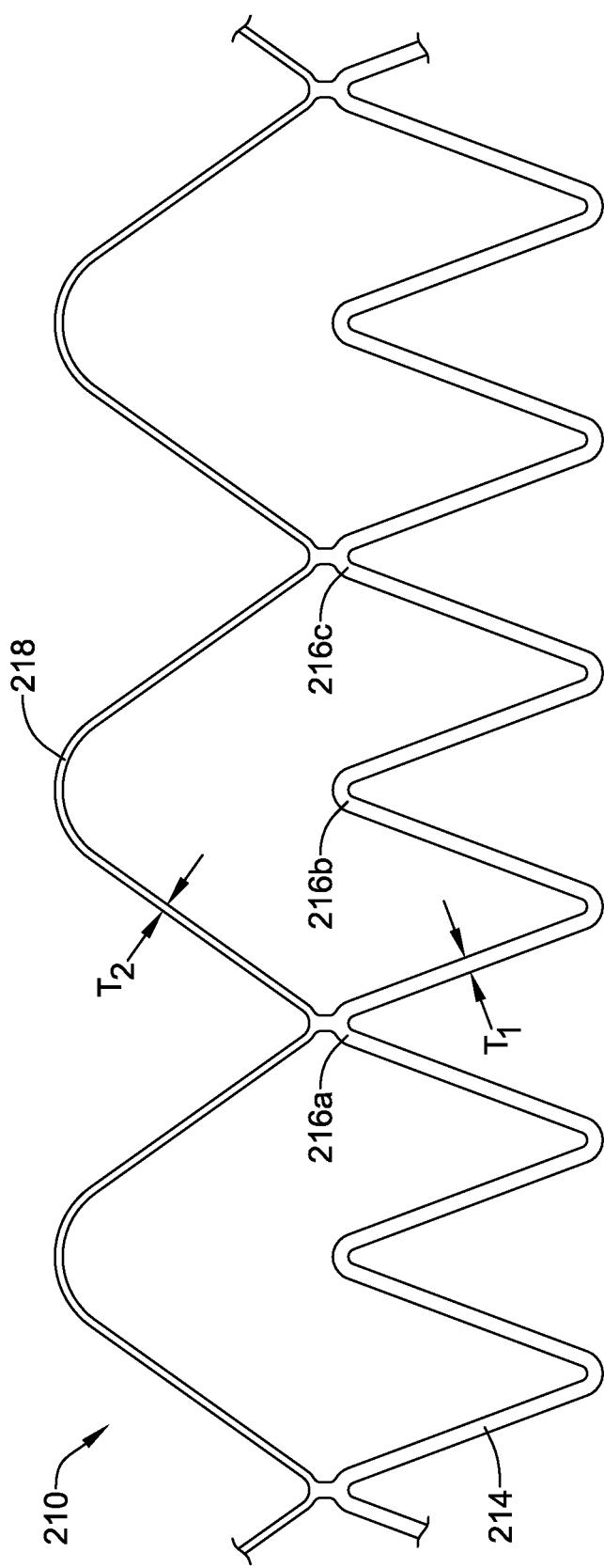
FIG. 4 is a side view of a portion of another example implantable medical device.

FIG. 4 illustrates a portion of another example stent 210 that may be similar in form and function to other stents disclosed herein. Stent 210 may include stent body 214 and nodes 216a/216b/216c. Cover member 218 may be coupled to body 214 much like cover member 118 is coupled to body 114. In some embodiments, one or more portions of body 214 may have an increased thickness relative to cover member 218. For example, body 214 may have a thickness T₁ (e.g., adjacent to one or more of nodes 216a/216b/216c) that is thicker than the thickness T₂ of cover member 218. The increased thickness may help reduce the number of pointed or sharpened edges along body 214.

Figure 5:
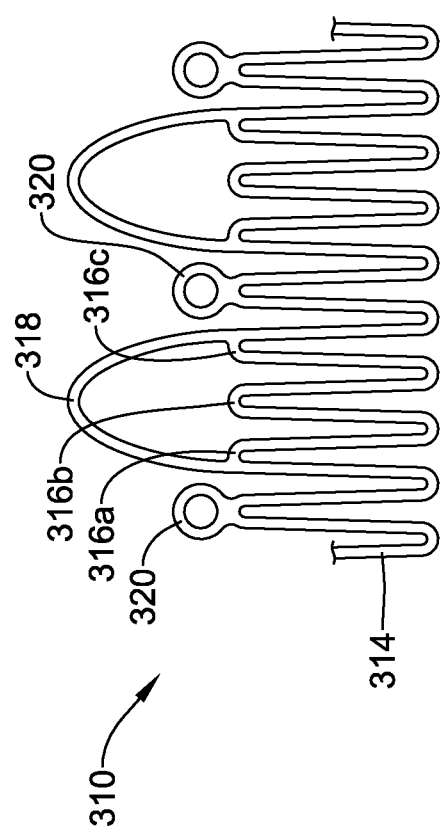
FIG. 5 is a side view of a portion of another example implantable medical device in a first configuration.
Figure 6:
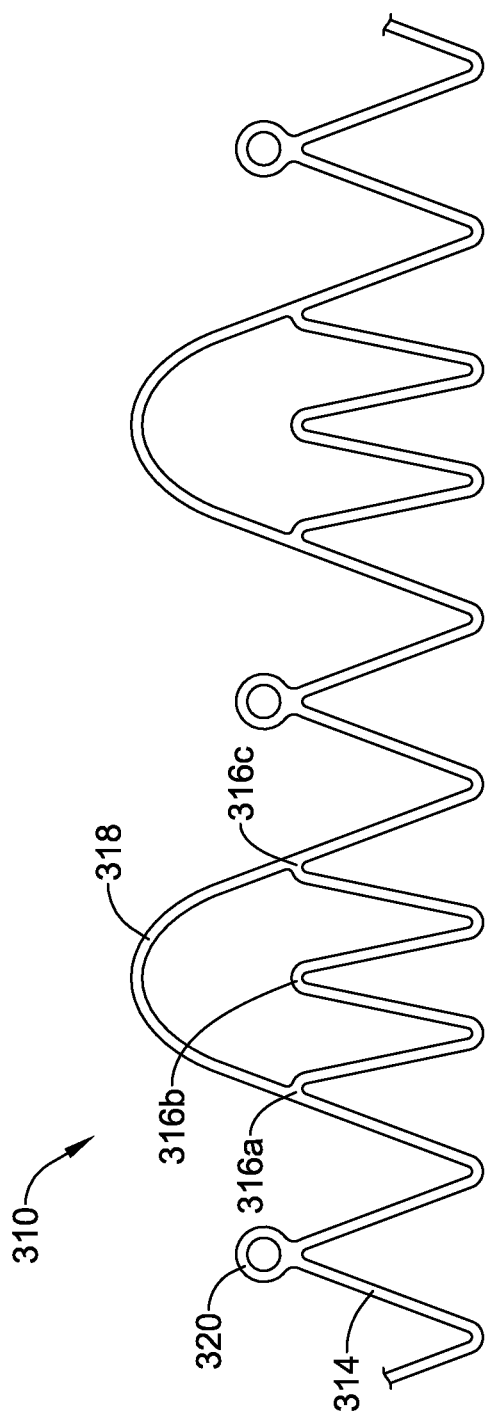
FIG. 6 is a side view of a portion of the example implantable medical device shown in FIG. 5 in a second configuration.

FIGS. 5-6 illustrate a portion of another example stent 310 that may be similar in form and function to other stents disclosed herein. In FIG. 5, stent 310 is shown in a first or "unexpanded" configuration. In FIG. 6, stent 310 is shown in a second or "expanded" configuration. Stent 310 may have stent body 314. Body 314 may define nodes 316a/316b/316c. Cover member 318 may be coupled to body 314. For example, cover member 318 may be attached to nodes 316a/316c and cover node 316b. Body 314 may also include one or more radiopaque nodes 320 that may include a radiopaque material. Node 320 may have a loop formed thereon. In some instances, node 320 may be formed from a radiopaque material. In other instances, a radiopaque material may be disposed within the loop formed at node 320.

Figure 7:
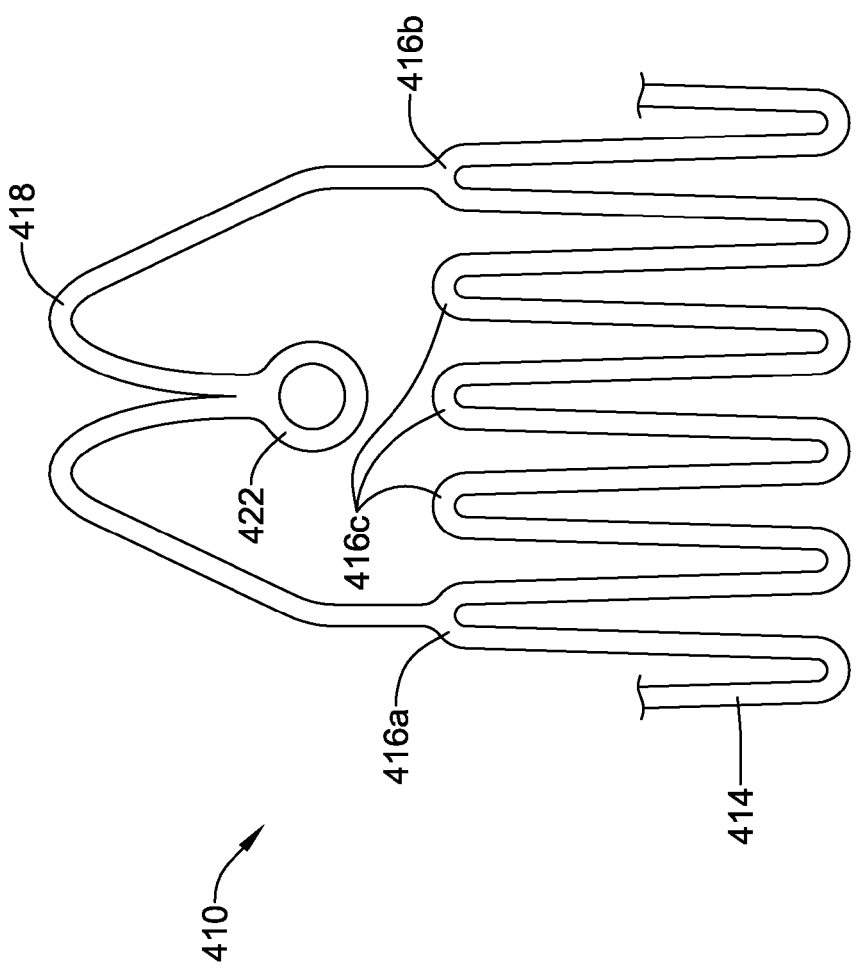
FIG. 7 is a side view of a portion of another example implantable medical device.

FIG. 7 illustrates a portion of another example stent 410 that may be similar in form and function to other stents disclosed herein. Stent 410 may include body 414 and nodes 416a/416b/416c. Cover member 418 may include a node 422. In this example, node 422 may have a looped configuration much like node 320. In at least some embodiments, node 422 may include a radiopaque material.

Figure 8:
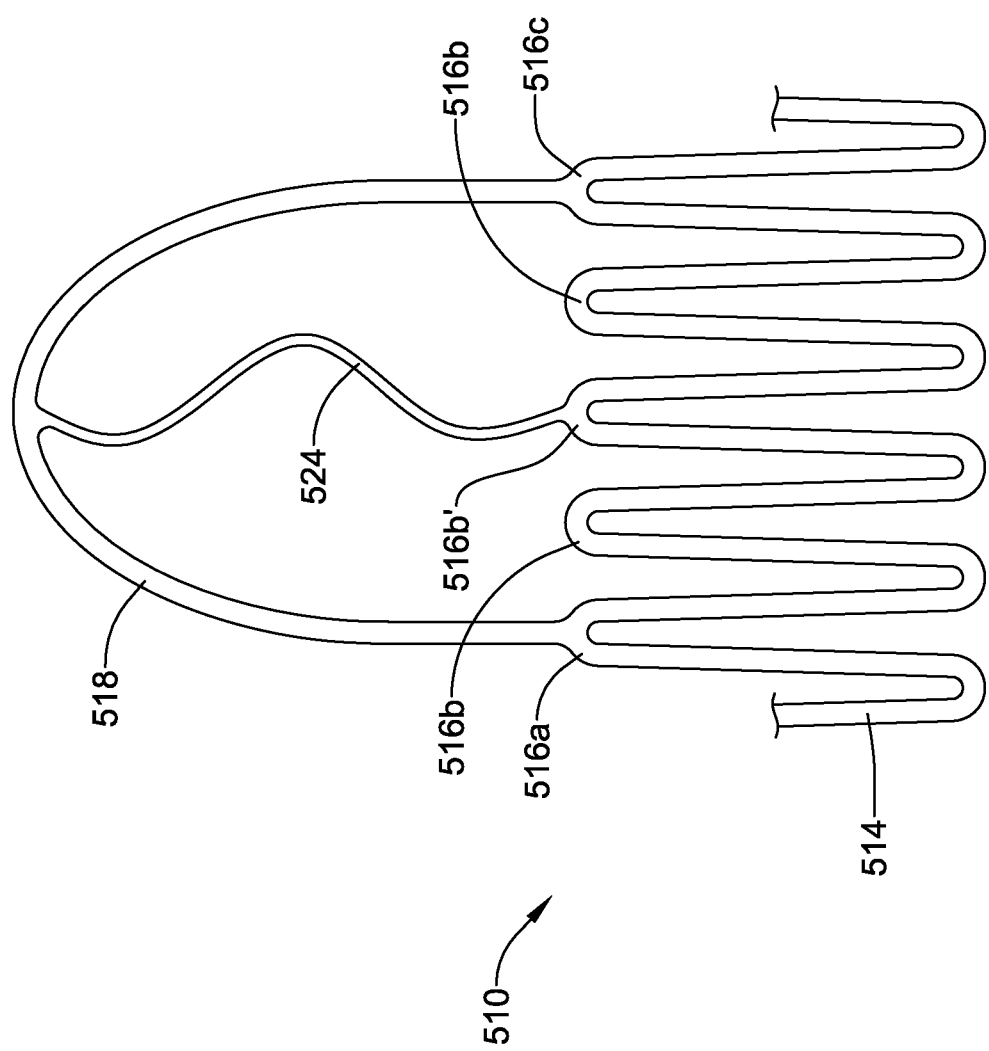
FIG. 8 is a side view of a portion of another example implantable medical device.

FIG. 8 illustrates a portion of another example stent 510 that may be similar in form and function to other stents disclosed herein. Stent 510 may include body 514 and nodes 516a/516b/516c. Cover member 518 may include a connector 524. Connector 524 may be attached to one of nodes 516a/516b/516c such as node 516b'. In general, connector 524 may help maintain the position of cover member 518 relative to body 514.

Figure 9:
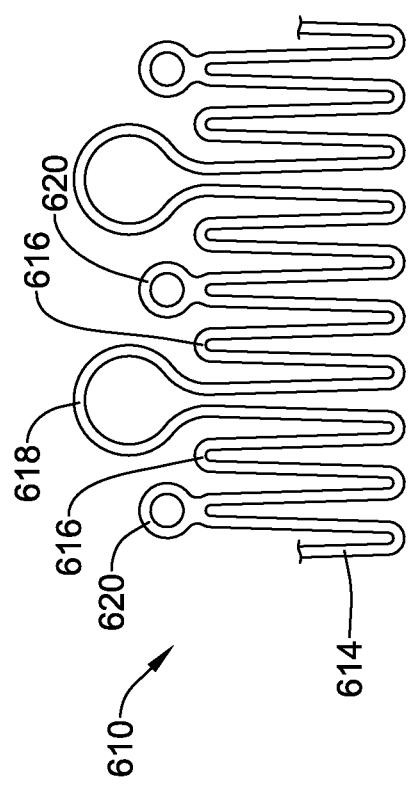
FIG. 9 is a side view of a portion of another example implantable medical device in a first configuration.
Figure 10:
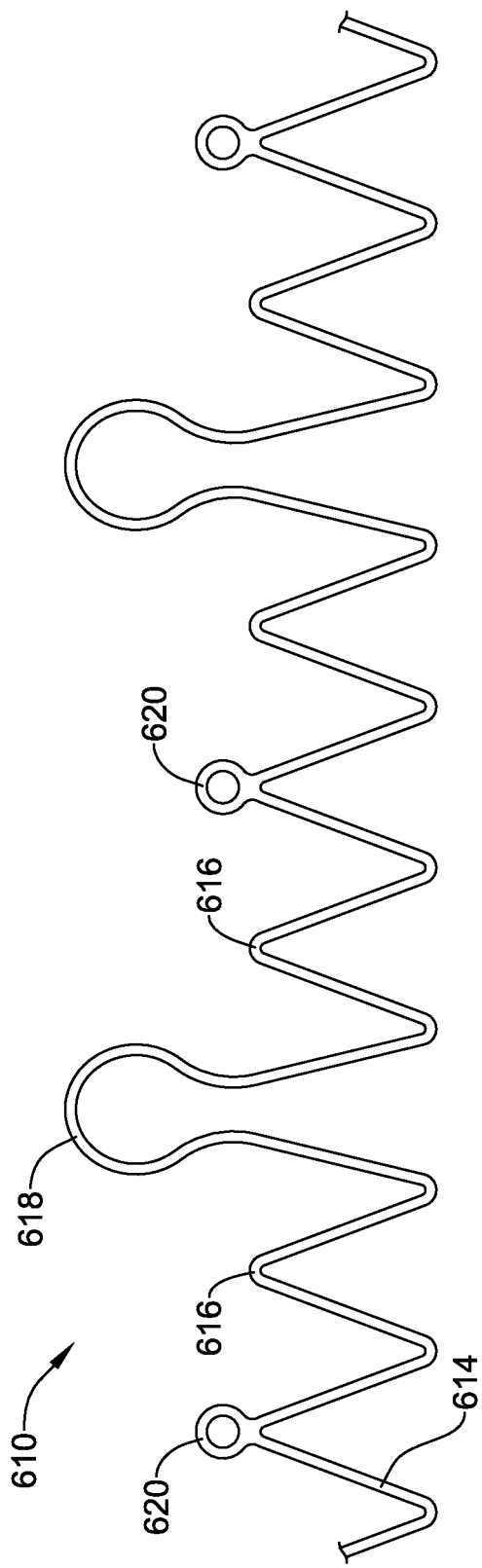
FIG. 10 is a side view of a portion of the example implantable medical device shown in FIG. 9 in a second configuration.

FIGS. 9-10 illustrate a portion of another example stent 610 that may be similar in form and function to other stents disclosed herein. In FIG. 9, stent 610 is shown in a first or "unexpanded" configuration. In FIG. 10, stent 610 is shown in a second or "expanded" configuration. Stent 610 may have stent body 614. Body 614 may define nodes 616. Cover member 618 may be coupled to body 614. In this example, rather than being a looped structure that extends between adjacent nodes, cover member 618 is formed at a position where a node may otherwise be defined. When stent 610 is expanded, cover member 618 may expand so as to cover adjacent nodes 616. Body 614 may also include one or more radiopaque nodes 620 that may include a radiopaque material.

Figure 11:
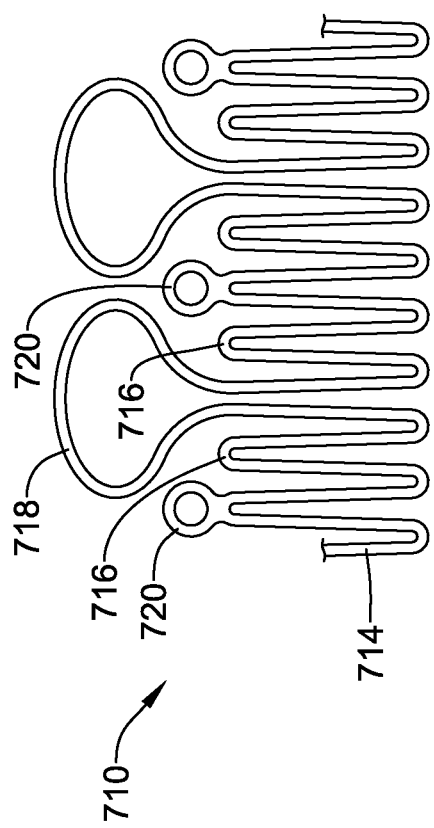
FIG. 11 is a side view of a portion of another example implantable medical device.

FIG. 11 illustrates a portion of another example stent 710 that may be similar in form and function to other stents disclosed herein. Stent 710 may have stent body 714. Body 714 may define nodes 716. Cover member 718 may be coupled to body 714. In at least some embodiments, cover member 718 may be similar to cover member 618 but may have an alternative shape. For example, cover member 618 may have a rounded shape whereas cover member 718 may have a more oval shape. These embodiments illustrate that a variety of different shapes may be utilized for cover members 618/718. Body 714 may also include one or more radiopaque nodes 720 that may include a radiopaque material.

Figure 12:
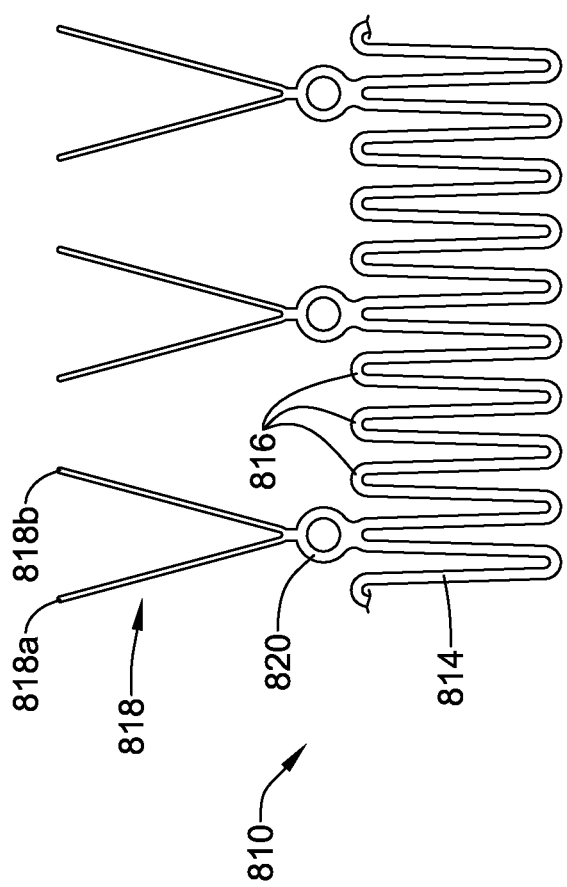
FIG. 12 is a side view of a portion of another example implantable medical device in a first configuration.
Figure 13:
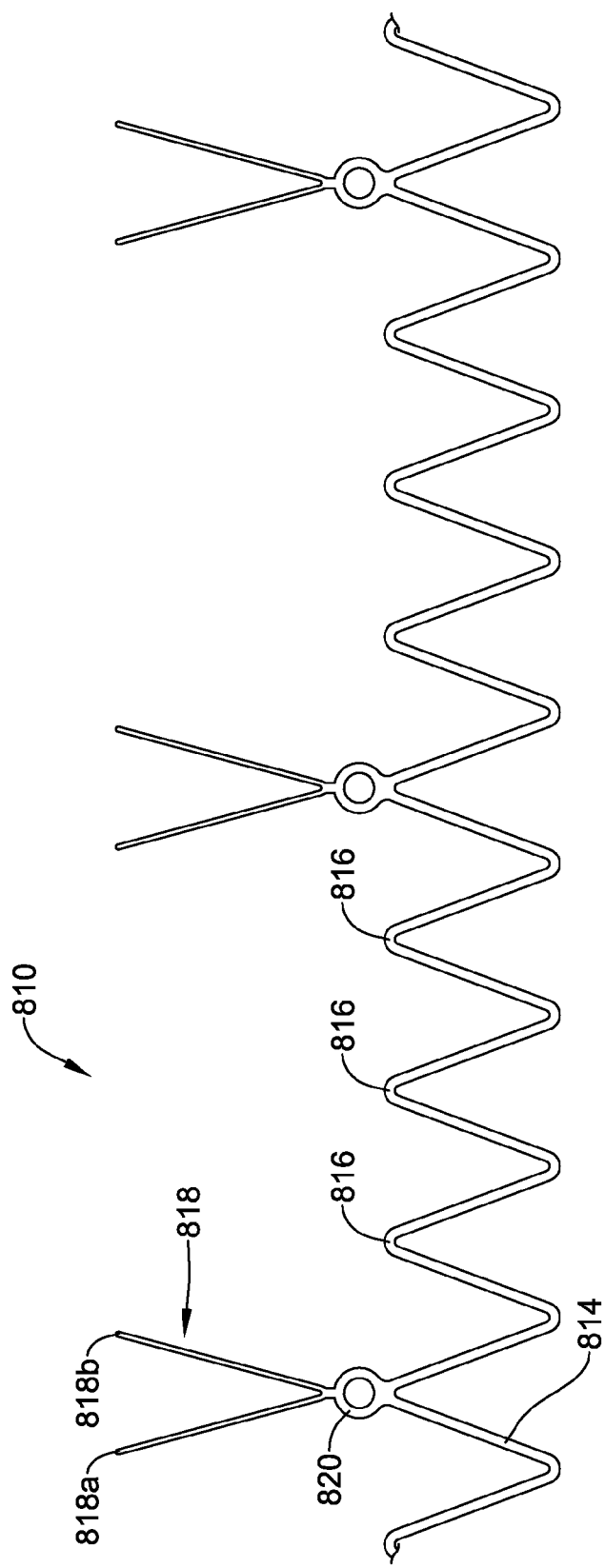
FIG. 13 is a side view of a portion of the example implantable medical device shown in FIG. 12 in a second configuration.
Figure 14:
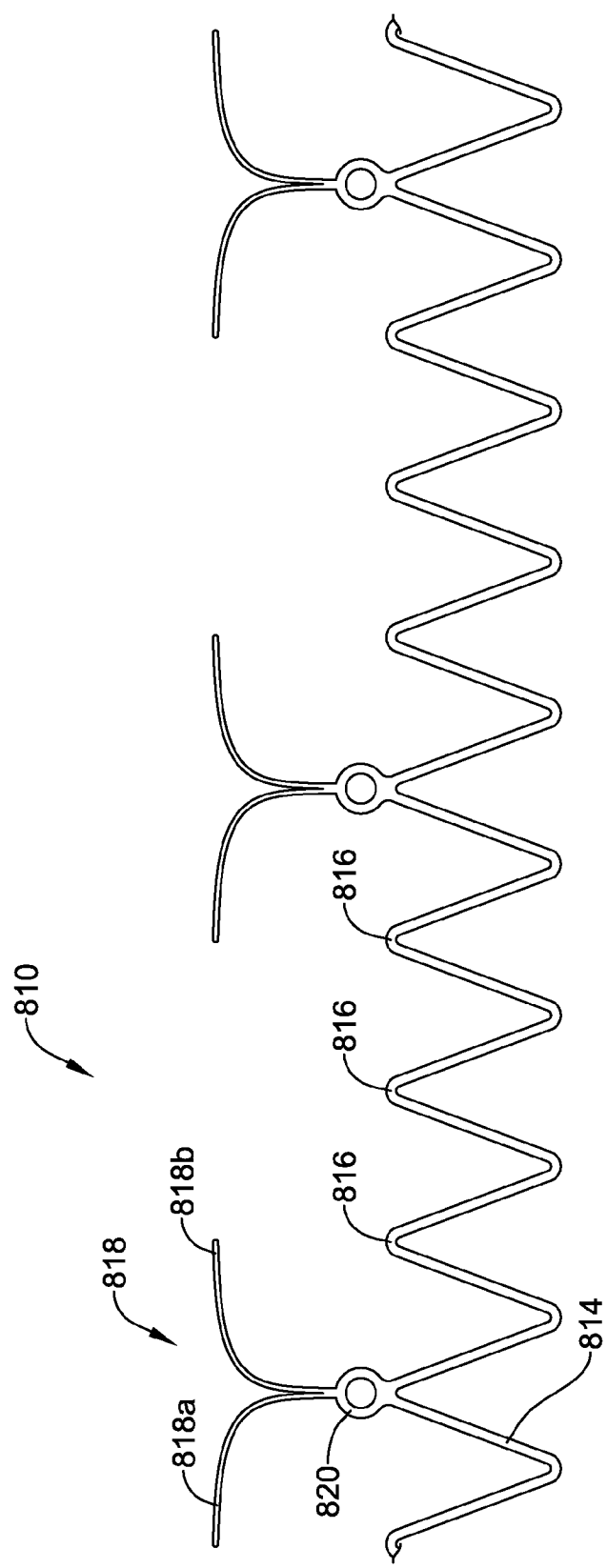
FIG. 14 is a side view of a portion of the example implantable medical device shown in FIG. 12 in a third configuration.

FIGS. 12-14 illustrate a portion of another example stent 810 that may be similar in form and function to other stents disclosed herein. In FIG. 12, stent 810 is shown in a first or "unexpanded" configuration. In FIG. 13, stent 810 is shown in a second or "expanded" configuration. In FIG. 14, stent 810 is shown in a third "expanded and formed" configuration.

Stent 810 may have stent body 814. Body 814 may define nodes 816. Cover member 818 may be coupled to body 814, for example at radiopaque node 820. However, in other embodiments cover member 818 may be coupled to body 814 at different locations. Cover member 818 may include a plurality of arms such as arms 818a/818b. Arms 818a/818b may be configured to be bent or otherwise formed into a configuration suited to cover one or more nodes 816. In some embodiments, arms 818a/818b may be formed using a forming mandrel or the like following the expansion of stent 810.

Figure 15:
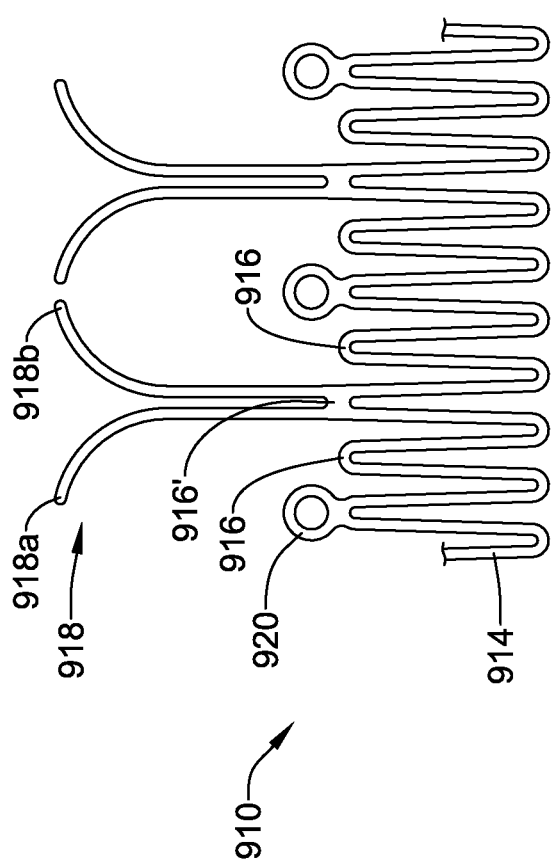
FIG. 15 is a side view of a portion of another example implantable medical device in a first configuration.
Figure 16:
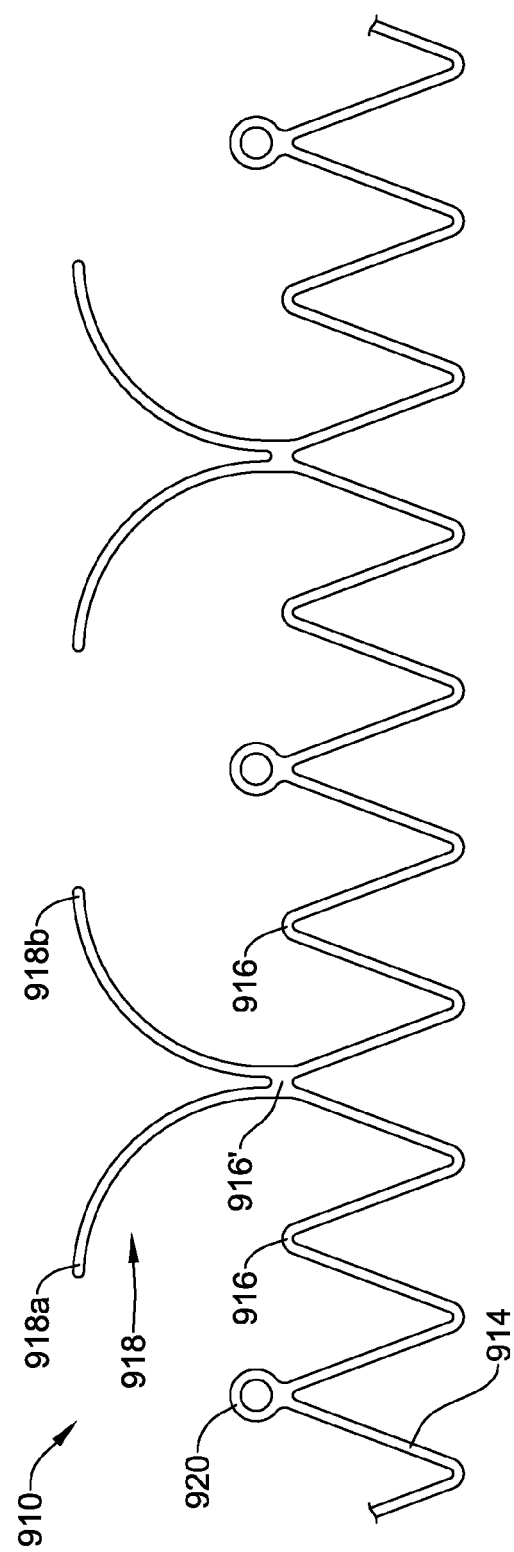
FIG. 16 is a side view of a portion of the example implantable medical device shown in FIG. 15 in a second configuration.

FIGS. 15-16 illustrate a portion of another example stent 910 that may be similar in form and function to other stents disclosed herein. In FIG. 15, stent 910 is shown in a first or "unexpanded" configuration. In FIG. 16, stent 910 is shown in a second or "expanded" configuration. Stent 910 may have stent body 914. Body 914 may define nodes 916. Cover member 918 may be coupled to body 914. For example, cover member 918 may be coupled to a node 916'. Cover member 918 may include a plurality of arms such as arms 918a/918b. Body 914 may also include one or more radiopaque nodes 920 that may include a radiopaque material.

Figure 17:
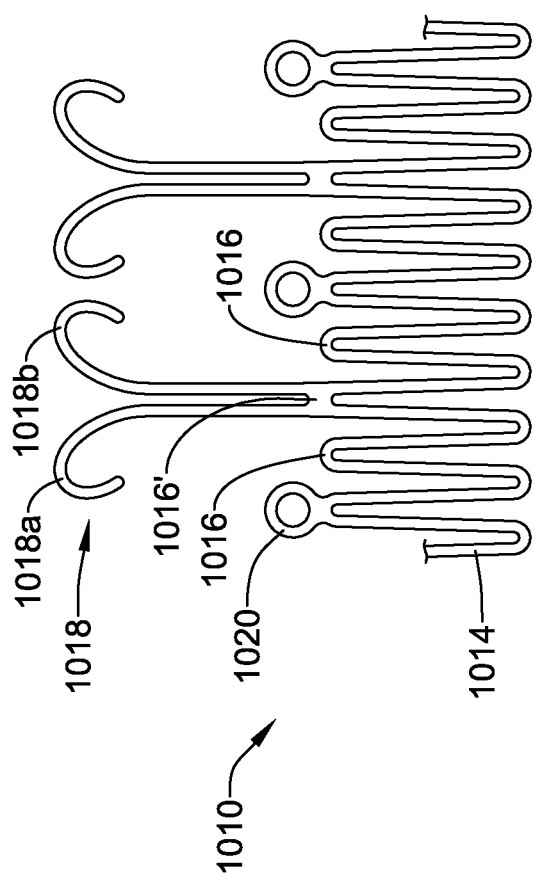
FIG. 17 is a side view of a portion of another example implantable medical device.

FIG. 17 illustrates a portion of another example stent 1010 that may be similar in form and function to other stents disclosed herein. Stent 1010 may have stent body 1014. Body 1014 may define nodes 1016. Cover member 1018 may be coupled to body 1014. For example, cover member 1018 may be coupled to node 1016'. Cover member 1018 may include a plurality of arms such as arms 1018a/1018b. Body 1014 may also include one or more radiopaque nodes 1020 that may include a radiopaque material.

The materials that can be used for the various components of stent 110 (and/or other stents disclosed herein) may include those commonly associated with medical devices. For simplicity purposes, the following discussion makes reference to stent 110. However, this is not intended to limit the devices and methods described herein, as the discussion may be applied to other similar stents including those disclosed herein.

Stent 110 may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of stent 110 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of stent 110 in determining its location. Some examples of radiopaque materials can include, but are not limited to, gold, platinum, palladium, tantalum, tungsten alloy, polymer material loaded with a radiopaque filler, and the like.

In some embodiments, a degree of Magnetic Resonance Imaging (MRI) compatibility is imparted into stent 110. For example, stent 110 may be made of a material that does not substantially distort the image and create substantial artifacts (i.e., gaps in the image). Certain ferromagnetic materials, for example, may not be suitable because they may create artifacts in an MRI image. Stent 110 may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An implantable medical device, comprising:
   a stent having a first configuration and a second expanded configuration;
   wherein the stent defines a plurality of adjacent nodes arranged circumferentially around the stent;
   wherein the stent has a plurality of cover members attached to at least some of the plurality of adjacent nodes and extending axially to a first end of the stent from the at least some of the plurality of adjacent nodes; and
   wherein each of the plurality of cover members is configured to cover at least some of the plurality of adjacent nodes when the stent is in the expanded configuration;
   wherein the plurality of adjacent nodes includes a node consisting of a radiopaque node loop attached to the node and extending axially toward the first end of the stent from the node, the radiopaque node loop being disposed entirely between adjacent cover members and not directly attached to any of the plurality of cover members.

2. The implantable medical device of claim 1, wherein the stent includes a first node and a second node, and wherein one or more of the plurality of nodes are disposed between the first node and the second node.

3. The implantable medical device of claim 2, wherein the first node, the second node, or both include a radiopaque material.

4. The implantable medical device of claim 2, wherein one of the cover members extends between the first node and the second node.

5. The implantable medical device of claim 2, wherein one of the cover members is disposed between the first node and the second node.

6. An expandable stent, comprising:
a stent body having a plurality of stent sections, wherein each stent section comprises:
  a plurality of consecutive elongate members defining sequential peaks and valleys formed by adjacent elongate members,
  wherein first and second consecutive elongate members converge at a first peak to form a first node of the stent body, third and fourth consecutive elongate members converge at a second peak to form a second node of the stent body, and fifth and sixth consecutive elongate members converge at a third peak to form a third node of the stent body, and
  a cover member extending between the first node and the third node and to a first end of the stent body;
  wherein the second and third consecutive elongate members converge at a first valley, and the fourth and fifth consecutive elongate members converge at a second valley;
  wherein the second node is positioned between the first node and the third node such that the cover member extends over and covers the second node;
the stent body further including seventh and eighth consecutive elongate members converging at a fourth peak to form a fourth node;
wherein the fourth node is disposed between adjacent stent sections and consisting of a radiopaque node loop attached to the fourth node, the radiopaque node loop extending from the fourth node toward the first end of the stent body.

\* \* \* \* \*